United States Patent [19]

Kopp

[11] 4,073,297
[45] Feb. 14, 1978

[54] CATHETER

[75] Inventor: Klaus F. Kopp, Kirchseeon, Germany

[73] Assignee: Sandoz Ltd., Basel, Switzerland

[21] Appl. No.: 657,093

[22] Filed: Feb. 11, 1976

[51] Int. Cl.$^2$ .................... A61M 5/14; A61M 25/00
[52] U.S. Cl. ................ 128/214.4; 128/221; 128/349 R; 128/DIG. 16
[58] Field of Search .......... 128/214.4, 215, 221, 128/DIG. 16, 348–351

[56] References Cited

U.S. PATENT DOCUMENTS

| | | | |
|---|---|---|---|
| 3,520,298 | 7/1970 | Lange | 128/348 X |
| 3,547,119 | 12/1970 | Hall et al. | 128/214.4 |
| 3,633,579 | 1/1972 | Alley et al. | 128/214.4 |
| 3,633,585 | 1/1972 | McDonald, Jr. | 128/348 |
| 3,875,938 | 4/1975 | Mellor | 128/214.4 |
| 3,877,429 | 4/1975 | Rasumoff | 128/DIG. 16 X |

*Primary Examiner*—Stephen C. Pellegrino
*Attorney, Agent, or Firm*—Gerald D. Sharkin; Robert S. Honor; Walter F. Jewell

[57] ABSTRACT

The invention concerns a novel catheter for placement in an artery, vein or fistula vessel of a patient, through which blood may be withdrawn or delivered to the patient, which comprises a catheter wall, the inside surface of which defines a lumen having a cross-sectional area in a proximal end region of the catheter which is larger than the cross-sectional area of the lumen defined in a distal end region of the catheter, at least one opening being provided in the wall of the catheter in the region of its distal end through which blood may be passed.

Various catheter assemblies employing a catheter such as described above are disclosed.

7 Claims, 3 Drawing Figures

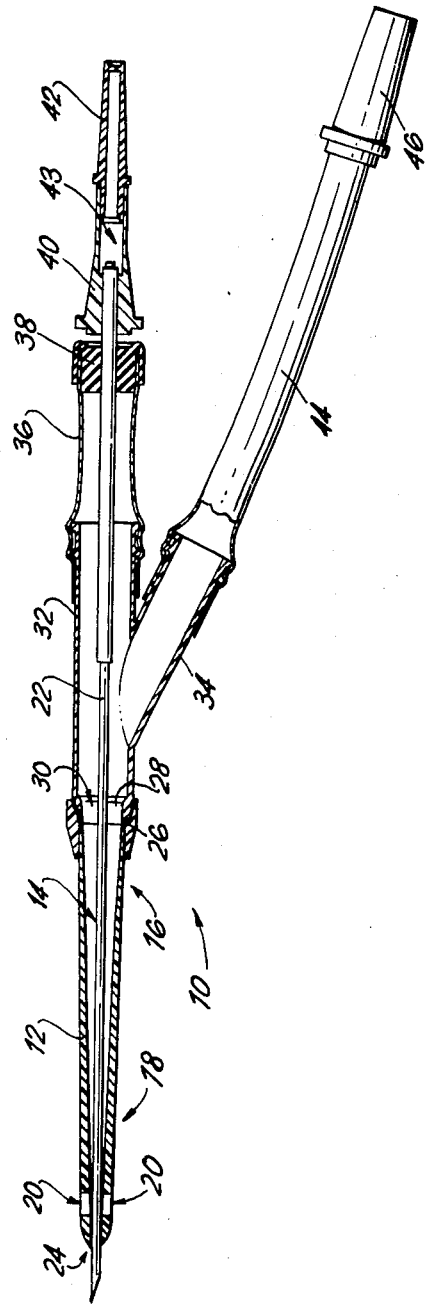
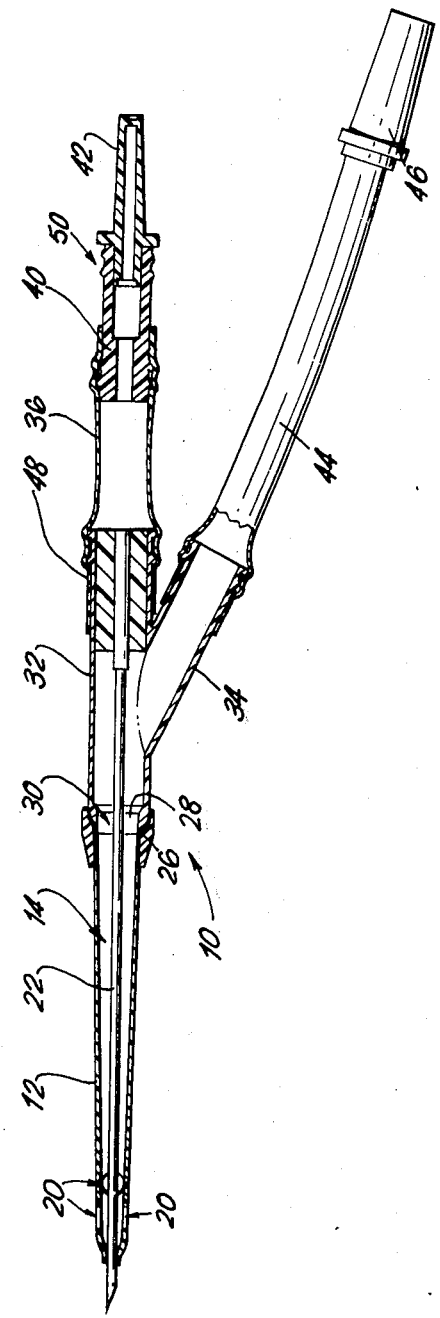

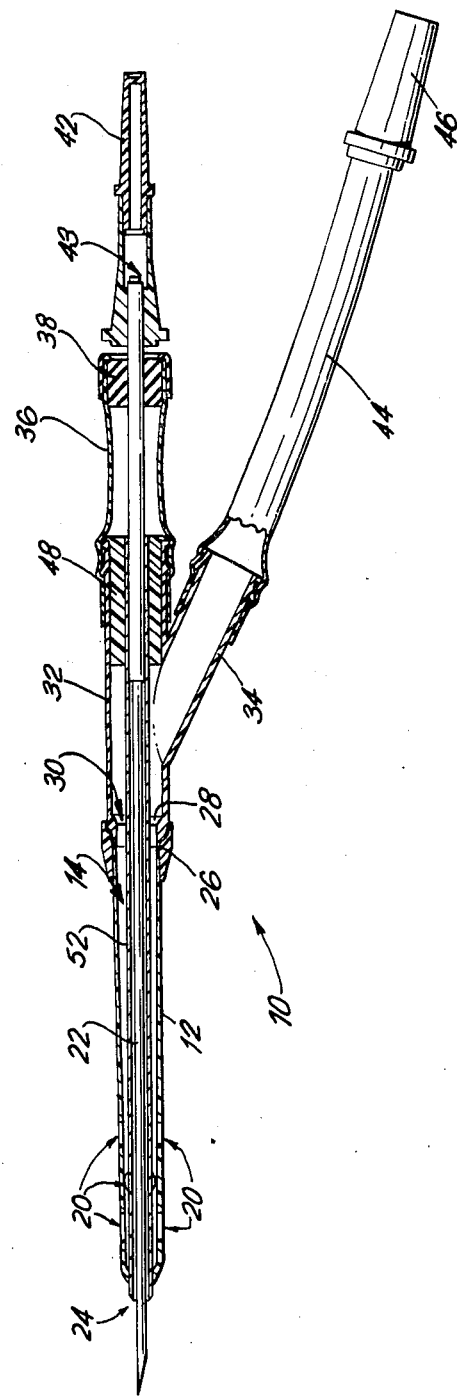

CATHETER

This invention relates to a catheter. More particularly, the invention relates to a catheter for placement in an artery, vein or fistula vessel of a patient, through which blood may be withdrawn or delivered to a patient.

The catheter of the invention is particularly intended for use in blood dialysis, where it is of high importance to achieve optimal blood flow rates to and from the patient. In view of the need to employ catheters of limited cross-sectional size, the catheter is normally the element in the entire extracorporeal blood flow path which plays the greatest role in limiting blood flow rates which can be achieved. This is particularly true in single needle dialysis, and there is indeed still some prejudice against employing the single needle dialysis technique for this reason.

Various catheters for effecting dialysis are available. These catheters normally comprise an open-ended length of catheter defining a lumen, about 1 to 1½ inches long, and a removable trocar located coaxially in the lumen with its point protruding beyond the distal end of the catheter. The trocar normally fits snugly against the inner wall surface of the catheter along its length but not so tightly that the trocar cannot be removed after placement of the catheter. The same applies to catheters intended for single needle dialysis, the removable trocar and catheter in this case being of somewhat larger cross section.

It has now been found that the flow rate of blood through catheters of the type described above can be significantly increased by modifying the form of the catheter, or rather the shape of the lumen defined by the catheter. Alternatively spoken, the same flow rate of blood can be achieved through the modified catheter when applying a significantly lower pressure differential to blood being withdrawn or returned to a patient.

The modification of the invention has wide application and may be employed in various types of catheters through which blood may be withdrawn or delivered to a patient. Catheters of various types to which the modification of the invention has been applied will be described below, more particularly with reference to the accompanying drawings.

In accordance with the invention, there is provided a catheter for placement in an artery, vein or fistula vessel of a patient, through which blood may be withdrawn or delivered to the patient, which comprises a catheter wall, the inside surface of which defines a lumen having a cross-sectional area in a proximal end region of the catheter which is larger than the cross-sectional area of the lumen defined in a distal end region of the catheter, at least one opening being provided in the wall of the catheter in the region of its distal end through which blood may be passed.

The cross-sectional area of the lumen most preferably diminishes uniformly from the region of larger cross-sectional area to the region of smaller cross-sectional area. However, the cross-sectional area may diminish in step-wise fashion.

In most catherers involving the modification of the invention, the distal end of the inside surface of the catheter wall defines an opening through which blood may be passed into and out of a lumen. Additionally, at least one opening may be provided in the wall of the catheter in the distal end region thereof. Preferably, two to six openings are provided in the wall of the catheter. The openings may be in pairs and two to three pairs of openings may be provided in the wall of the catheter, the two openings of each pair preferably being in diametrically opposed relationship, each pair of hollows then being longitudinally spaced away from one another. Adjacent pairs of such diametrically opposed openings are preferably arranged at right angles to one another so that weakening of the distal end region of the catheter is minimised.

The one or more openings in the wall of the catheter are preferably provided in the distal end region where the cross-sectional area of the lumen is progressively diminishing towards the distal end of the catheter.

In one embodiment of a catheter in accordance with the invention, the total area of the openings in the walls of the catheter, together with the area defined by the distal end of the catheter, should be at least as great as the smallest cross-sectional area of the lumen through which blood may be passed. In another embodiment, the total area of the openings in the wall of the catheter (without the opening defined by the distal end of the catheter) should be at least as great as the cross-sectional area of the lumen.

For ease of insertion of the catheter, the outer diameter of the catheter most preferably diminishes to a minimum outer diameter at the distal end from a position distal to the distally most extreme opening in the wall of the catheter. Similarly, the cross-sectional area of the lumen most preferably diminishes to a minimum from the same position.

The proximal end of the catheter may be coaxially connected to a hub having a bore of cross-sectional area at least as large as the largest cross-sectional area of the lumen, the hub in turn being coaxially connected to a hollow cylindrical body having a closure at its free end.

The hollow cylindrical body may have a hollow cylindrical side arm leading into the side of the hollow cylindrical body. The free end of the side arm may be provided with means for connection to a blood line or the free end of the side arm may alternatively be sealed closed by a resealable plug through which a needle may be passed.

The catheter may be provided with a hollow needle (or removable trocar) which passes through the closure at the free end of the hollow cylindrical body and coaxially through the hollow cylindrical body, through the hub and through the catheter so that the point of the needle protrudes beyond the distal end of the catheter. This hollow needle may be provided with female luer means at its proximal end for receiving the nose of a syringe.

The closure at the free end of the hollow cylindrical body may comprise a flexible tube coaxially connected to the free end of the hollow cylindrical body, and a removable resealable plug sealing closed the free end of the flexible tube and through which the needle passes.

The thickness of the catheter side wall is most preferably progressively greater from the region where the cross-sectional area of the lumen is larger to the region where the cross-sectional area of the lumen is smaller. In this manner a minimum outer diameter of the catheter in the proximal end region can be achieved.

The inner diameter of the catheter may range from about 0.02 to about 0.07 inches, preferably from about 0.03 to about 0.06 inches. The inner diameter of the needle may range from about 0.02 to about 0.05 inches, preferably from about 0.03 to about 0.04 inches.

The invention will now be described with reference to the accompanying drawings showing by way of example, catheter assemblies involving the modification of the invention.

In the drawings:

FIG. 1 shows a cross-sectional side elevation of a catheter assembly in which a removable trocar is provided;

FIG. 2 shows a cross sectional side elevation of a catheter assembly in which a needle defining an inner lumen is provided;

FIG. 3 shows a cross-sectional side elevation of a catheter assembly comprising first and second catheters, one located coaxially within the other and a removable trocar passing through the lumen defined by the inner catheter.

Referring to FIG. 1 of the drawings, reference numeral 10 refers generally to a catheter assembly comprising a catheter wall 12, the inside surface of which defines a lumen 14. The lumen 14 has a cross-sectional area in a proximal end region 16 of the catheter which is larger than the cross-sectional area of the lumen 14 defined in a distal end region 18 of the catheter. A pair of diametrically opposed openings 20 are provided in the wall 12 of the catheter in the distal end region 18. It will be noted that the cross-sectional area of the lumen 14 diminishes substantially uniformly from the proximal end region 16 (of larger cross-sectional area) to the distal end region 18 (of smaller cross-sectional area).

Reference numeral 22, in FIG. 1, refers to a hollow needle or trocar which is removable. The distal end of the inside surface of the catheter wall 12 defines an opening 24 when the trocar 22 is removed. With the trocar 22 removed, blood may be passed into and out of the lumen when the catheter is placed in an artery, vein or fistula vessel of a patient by means of a monitoring and blood pump device (not shown).

The pair of openings 20 in the wall 12 of the catheter are in a region where the cross-sectional area of the lumen 14 is diminishing towards the distal end of the catheter. The total area of the openings 20 in wall 12 of the catheter, together with the area of the opening 24 defined by the distal end of the catheter (with trocar 22 removed), should be at least as great as the smallest cross-sectional area of the lumen 14.

Still referring to FIG. 1, the proximal end 26 of the catheter is coaxially connected to a hub 28 having a bore 30 which is as large as the largest cross-sectional area of the lumen 14 (in the proximal end region 16). The hub 28 is in turn coaxially connected to a hollow cylindrical body 32 having a hollow cylindrical side arm 34 leading into its side. A flexible tube 36 carrying a removable resealable plug 38 is connected to the end of the hollow cylindrical body 32. The removable trocar 22 passes through the plug 38, through the flexible tube 36, coaxially through the hollow cylindrical body 32, through the hub 28 and through the catheter so that the point of the trocar protrudes beyond the distal end of the catheter.

A female luer 40 is mounted at the proximal end of the trocar 22, which is kept closed by a removable closure cap 42. The female luer defines a bore 43 into which the nose of an infusion syringe may be fitted.

A short length of flexible tubing 44, carrying a closure cap 46, is connected to the end of the side arm 34.

The embodiment of a catheter assembly shown in FIG. 1 is suitable both for so-called single needle dialysis and for double needle dialysis. For double needle dialysis, the catheter may be somewhat smaller in cross-section, and a resealable plug similar to resealable plug 38 is then conveniently provided to close off the end of the side arm 34. Such resealable plug may serve as an infusion point.

Referring now to FIGS. 2 and 3 of the drawings, reference numerals 10 to 46 refer to the same integers of the catheter assembly as in FIG. 1.

Referring now particularly to FIG. 2 of the drawings, the needle 22 is not removable as in the trocar of FIG. 1. Furthermore, the needle terminates at the end of the hollow cylindrical body 32 and is sealed at this end to the wall of the hollow cylindrical body 32 by means of a seal 48. The female luer 40, instead of being mounted on the needle as in FIG. 1, is somewhat different in form and is fitted into the end of the flexible tube 36. The end of the female luer adjacent the closure cap 42 is connectable at 50 to a blood line. Another difference between the assembly shown in FIG. 2 and that shown in FIG. 1 is the form of the catheter towards its distal end region 18. Thus, the wall 12 of the catheter is spaced away from the outer surface of the needle 22 in said distal end region. Four openings 20 are provided in said distal end region 18, and the catheter then converges towards its distal end to seal against the outer wall of the needle. Blood may thus pass into the lumen 14 through openings 20. In this construction two pairs of diametrically opposed openings 20 are provided, the one pair being at right angles to the other.

FIG. 3 comprises features common to both FIGS. 1 and 2. Thus, the removable trocar 22 of FIG. 1 is provided, and the needle 22 of FIG. 2 (which is not removable) is replaced by an inner catheter 52 which, when the trocar 22 is removed, defines an inner lumen. The lumen 14 in FIG. 3 is in the form of an annular outer lumen which is defined between the outer surface of the inner catheter 52 and the inner surface of the catheter (outer) 12. In this construction, three pairs of diametrically opposed openings 20 are provided, each pair being arranged at right angles to one another.

In the embodiments shown in both FIGS. 2 and 3, the cross-section of the bore 30 of the hub 28 is at least as great as the sum of the outer cross-sectional area of the needle 22 (in FIG. 2) or the inner catheter 52 (in FIG. 3) and the largest cross-sectional area of th the annular outer lumen 14 (in both FIGS. 2 and 3).

In operation of the embodiment shown in FIG. 1, the vein, artery or fistula vessel is punctured by means of the trocar 22, and the catheter is inserted into the vessel to a point near the proximal end region 16. Infusion may be effected through the trocal 22 during this placement. The trocar is then partly withdrawn, and blood is allowed to fill the lumen 14, hollow cylindrical body 32 and flexible tube 36. The trocar is then completely withdrawn, the flexible tube 36 clamped closed, the removable resealable plug 38 removed and the end of the flexible tube 36 connected up to a blood line leading to the monitoring and blood pump device (not shown). Similarly, the short length of flexible tubing 44 connected to the side arm 34 is clamped closed, the cap 46 removed and connected up to a blood line leading from the monitoring and blood pump device.

In operation of the embodiment shown in FIG. 2, the catheter is similarly placed in an artery, vein or fistula vessel of a patient, but in this case the needle 20 is not withdrawn since it serves the function of defining an inner lumen through which blood may be returned to the patient, blood being withdrawn through the lumen 14 (outer) and to the monitoring and pump device through the side arm 34.

Operation of the embodiment shown in FIG. 3 is similar to that of FIG. 2, excepting that the trocar 22 is removed and connection up to the blood line is effected as described in relation to FIG. 1.

What is claimed is:

1. A catheter for placement in an artery, vein or fistula vessel of a patient, through which blood may be withdrawn or delivered to the patient, which comprises a catheter defining an outer lumen having a cross-sectional area in a proximal end region of the catheter which is larger than the cross-sectional area of the outer lumen in a distal end region of the catheter, at least one opening being provided in the wall of the catheter in the distal end region thereof, a hub having a bore, connected coaxially to the proximal end of the catheter, a hollow cylindrical body coaxially connected to the hub and having connection means at its free end, for connection to a blood line, a hollow cylindrical side arm leading into the side of the hollow cylindrical body and having means for connection to a blood line, a hollow needle defining an inner lumen through which blood may be delivered to the patient which passes coaxially through the hollow cylindrical body, through the hub and through the catheter so that the point of the needle protrudes beyond the distal end of the catheter, the cross-sectional area of the outer lumen diminishing to a minimum cross-sectional area at the distal end of the catheter from a position distal to the distally most extreme opening in the wall of the catheter, said minimum cross-sectional area of the outer lumen corresponding to the outer cross-sectional area of the needle so that the distal end of the catheter seals against the wall of the needle, an annular outer lumen in communication with the hollow cylindrical body and the hollow cylindrical side arm thereby being defined by the inner surface of the catheter and by the outer surface of the needle, which annular outer lumen progressively increases in cross-sectional area rearwardly towards the proximal end of the catheter from the distal end region, the cross-sectional area of the bore of the hub being at least as large as the sum of the outer cross-sectional area of the needle and the largest cross-sectional area of said annular outer lumen.

2. A catheter for placement in an artery, vein or fistula vessel of a patient, through which blood may be withdrawn or delivered to the patient, which comprises a catheter side wall, the inside surface of which defines a lumen having a cross-sectional area in a proximal end region of the catheter which is larger than the cross-sectional area of the lumen defined in a distal end region of the catheter where the cross-sectional area of the lumen progressively diminishes to a minimum at the distal end of the catheter, at least one side opening being provided in the wall of the catheter in said distal end region, and an end opening defined by the distal end of the inside surface of the catheter wall, the thickness of the catheter side wall being progressively greater from the region where the cross-sectional area of the luman is larger to the region where the cross-sectional area of the lumen is smaller.

3. A catheter for placement in an artery, vein or fistula vessel of a patient, through which blood may be withdrawn and delivered to the patient, which comprises a first catheter defining an outer lumen having a cross-sectional area in a proximal end region of said first catheter which is larger than the cross-sectional area of the outer lumen in a distal end region of said first catheter, at least one opening being provided in the wall of said first catheter in the distal end region thereof, a second catheter defining an inner lumen coaxially within the outer lumen and in which the distal end of said second catheter defines an opening through which blood may be passed, the cross-sectional area of the outer lumen diminishing to a minimum cross-sectional area at the distal end of the catheter from a position distal to the distally most extreme opening in the wall of the first catheter, said minimum cross-sectional area of the outer lumen corresponding to the outer cross-sectional area of the second catheter so that the distal end of the first catheter seals against the wall of the second catheter, an annular outer lumen through which blood may be withdrawn from the patient thereby being defined by the inner surface of the first catheter and by the outer surface of the second catheter, which annular outer lumen progressively increases in cross-sectional area rearwardly towards the proximal end of the first catheter from the distal end region thereof.

4. A catheter according to claim 3, in which a removable trocar is located in said second catheter so that the point of the needle protrudes through the opening defined by the distal end of said second catheter.

5. A catheter according to claim 3, in which the second catheter defines an inner lumen having cross-sectional area in a proximal end region thereof which is larger than the cross-sectional area of the inner lumen in a distal end region thereof.

6. A catheter according to claim 3, additionally comprising a hub having a bore, connected coaxially to the proximal end of said first catheter, a hollow cylindrical body coaxially connected to the hub and having a removable closure and means for connection to a blood line at its free end, a hollow cylindrical side arm leading into the side of the hollow cylindrical body having means at its free end for connection to a blood line, said second catheter leading rearwardly from its distal end through the bore of the hub and to the free end of the hollow cylindrical body where the outer surface of the wall of the second catheter is sealed against the inner surface of the wall of the hollow cylindrical body so that an annular blood flow passage in communication with said annular outer lumen and the hollow cylindrical side arm is defined by the outer surface of the wall of the second catheter and the inner surface of the wall of the hollow cylindrical body, a removable trocar which passes through the removable closure at the free end of the hollow cylindrical body and coaxially through the second catheter so that the point of the trocar protrudes beyond the distal end of the catheter, the cross-sectional area of the bore of the hub being at least as large as the sum of the outer cross-sectional area of the second catheter where it passes through the bore of the hub and the largest cross-sectional area of said annular outer lumen.

7. A catheter according to claim 6, in which the removable closure and means for connection to a blood line comprises a flexible tube coaxially connected to the free end of the hollow cylindrical body, and a removable resealable plug sealing closed the free end of the flexible tube and through which the removable trocar passes.

* * * * *